US008585938B1

(12) United States Patent
Jinkerson et al.

(10) Patent No.: US 8,585,938 B1
(45) Date of Patent: Nov. 19, 2013

(54) UV-ABSORBERS FOR OPHTHALMIC LENS MATERIALS

(71) Applicant: Novartis AG, Basel (CH)

(72) Inventors: David L. Jinkerson, Benbrook, TX (US); Walter R. Laredo, Fort Worth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/853,222

(22) Filed: Mar. 29, 2013

Related U.S. Application Data

(60) Provisional application No. 61/618,174, filed on Mar. 30, 2012.

(51) Int. Cl.

| | |
|---|---|
| F21V 9/04 | (2006.01) |
| F21V 9/06 | (2006.01) |
| G02B 5/22 | (2006.01) |
| G02B 5/26 | (2006.01) |
| G02B 5/23 | (2006.01) |
| G02C 7/02 | (2006.01) |
| A61K 31/74 | (2006.01) |
| C07D 249/04 | (2006.01) |
| C07D 249/16 | (2006.01) |
| C07D 403/00 | (2006.01) |
| C09K 3/00 | (2006.01) |

(52) U.S. Cl.
USPC ... 252/589; 252/183.11; 252/586; 424/78.04; 514/912; 523/106; 523/107; 534/843; 534/852; 548/255; 548/257; 548/259; 548/260; 548/261; 623/6.11

(58) Field of Classification Search
USPC .............. 252/183.11, 586, 589; 424/78.04; 514/912; 523/106, 107; 534/843, 852; 548/255, 257, 259, 260, 261; 623/6.11
See application file for complete search history.

(56) References Cited

U.S. PATENT DOCUMENTS

| | | | |
|---|---|---|---|
| 4,716,234 | A | 12/1987 | Dunks et al. |
| 5,290,892 | A | 3/1994 | Namdaran et al. |
| 5,331,073 | A | 7/1994 | Weinschenk, III et al. |
| 5,470,932 | A | 11/1995 | Jinkerson |
| 5,528,322 | A | 6/1996 | Jinkerson |
| 5,543,504 | A | 8/1996 | Jinkerson |
| 5,637,726 | A | 6/1997 | Collins et al. |
| 5,662,707 | A | 9/1997 | Jinkerson |
| 5,693,095 | A | 12/1997 | Freeman et al. |
| 6,528,602 | B1 | 3/2003 | Freeman et al. |
| 6,806,337 | B2 | 10/2004 | Schlueter et al. |
| 6,846,897 | B2 | 1/2005 | Salamone et al. |
| 6,852,793 | B2 | 2/2005 | Salamone et al. |
| 6,872,793 | B1 | 3/2005 | Schlueter |
| 7,037,954 | B2 | 5/2006 | Baba et al. |
| 7,067,602 | B2 | 6/2006 | Benz et al. |
| 7,101,949 | B2 | 9/2006 | Salamone et al. |
| 7,119,210 | B2 | 10/2006 | Schlueter |
| 7,396,942 | B2 | 7/2008 | Schuleter |
| 7,691,918 | B2 | 4/2010 | Jinkerson et al. |
| 7,709,652 | B2 | 5/2010 | Schlueter |
| 7,728,051 | B2 | 6/2010 | Weinschenk, III et al. |
| 7,781,571 | B2 | 8/2010 | Weinschenk, III et al. |
| 7,803,359 | B1 | 9/2010 | Jinkerson et al. |
| 7,884,228 | B1 | 2/2011 | Laredo |
| 7,909,458 | B2 | 3/2011 | Schlueter |
| 7,947,849 | B2 | 5/2011 | Laredo |
| 8,043,607 | B2 | 10/2011 | Jinkerson |

(Continued)

Primary Examiner — Bijan Ahvazi
(74) Attorney, Agent, or Firm — Patrick M. Ryan

(57) ABSTRACT

UV absorbing compounds that are effective in blocking UV and short-wavelength blue light are disclosed. The UV absorbing compounds are particularly suitable for use in intraocular lens materials.

15 Claims, 1 Drawing Sheet

(56) References Cited

U.S. PATENT DOCUMENTS

| | | |
|---|---|---|
| 8,115,009 B2 | 2/2012 | Schlueter |
| 8,119,830 B2 | 2/2012 | Schlueter |
| 8,153,703 B2 | 4/2012 | Laredo |
| 8,207,244 B2 | 6/2012 | Laredo |
| 8,236,053 B1 | 8/2012 | Freeman |
| 8,262,947 B2 | 9/2012 | Laredo |
| 8,323,631 B2 | 12/2012 | Jinkerson |
| 8,329,775 B2 | 12/2012 | Laredo |
| 2006/0252850 A1 | 11/2006 | Jani et al. |
| 2013/0032757 A1 | 2/2013 | Jinkerson |

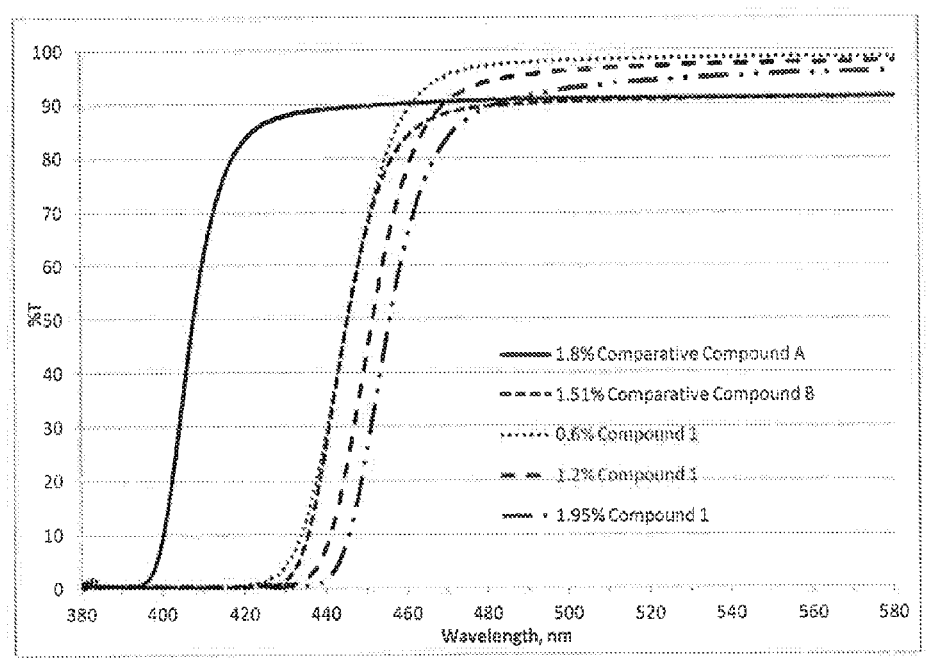

UV-ABSORBERS FOR OPHTHALMIC LENS MATERIALS

CROSS-REFERENCE TO RELATED APPLICATIONS

This application claims priority under 35 U.S.C. §119 to U.S. Provisional Patent Application No. 61/618,174, filed Mar. 30, 2012, the entire contents of which are incorporated herein by reference.

FIELD OF THE INVENTION

This invention is directed to ophthalmic lens materials. In particular, this invention relates to novel trifluoromethyl-substituted benzotriazole UV absorbers and their use in ophthalmic lens materials.

BACKGROUND OF THE INVENTION

Many UV light absorbers are known as ingredients for polymeric materials used to make ophthalmic lenses and, in particular, intraocular lenses. UV absorbers are preferably covalently bound to the polymeric network of the lens material instead of simply physically entrapped in the material to prevent the absorber from migrating, phase separating or leaching out of the lens material. Such stability is particularly important for implantable ophthalmic lenses where the leaching of the UV absorber may present both toxicological issues and lead to the loss of UV blocking activity in the implant.

Numerous copolymerizable benzatriazole, benzophenone and triazine UV absorbers are known. Many of these UV absorbers contain conventional olefinic polymerizable groups, such as methacrylate, acrylate, methacrylamide, acrylamide or styrene groups. Copolymerization with other ingredients in the lens materials, typically with a radical initiator, incorporates the UV absorbers into the resulting polymer chain. Incorporation of additional functional groups on a UV absorber may influence one or more of the UV absorber's UV absorbing properties, solubility or reactivity. If the UV absorber does not have sufficient solubility in the remainder of the ophthalmic lens material ingredients or polymeric lens material, the UV absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

In addition to blocking UV light, some ophthalmic lenses also block blue light. See, for example, U.S. Pat. Nos. 5,470,932 and 5,543,504. These lenses block both types of light by using two chromophores: a UV absorber and a yellow dye.

There is a need for UV absorbers that are suitable for use in implantable ophthalmic lenses and are capable of blocking not only UV light (400 nm and below) but also blocking at least some light between 400-450 nm.

SUMMARY OF THE INVENTION

The present invention provides UV absorbers that block not only UV light but also light in the 400-450 nm range. Transmission cutoffs from 1% T to 10% T in the 430 to 440 nm wavelength range can be achieved at concentrations from 1 to 2 wt. % in an ophthalmic device material. These UV absorbers are suitable for use in ophthalmic devices, including contact lenses, and are particularly useful in implantable lenses, such as intraocular lenses (IOLs). The UV absorbers of the present invention are copolymerizable with other ingredients in ophthalmic device formulations.

Specifically, the novel UV absorbers of the present invention contain the following combination of three structure features:
  i. 4'-alkoxy-substitution of 2-hydroxyphenyl moiety;
  ii. 3'-tertiary alkyl substitution of the 2-hydroxyphenyl moiety; and
  iii. 5-trifluoromethyl substitution of benzotriazole moiety.

BRIEF DESCRIPTION OF THE DRAWINGS

FIG. 1 shows the UV/VIS spectra of various UV absorbers.

DETAILED DESCRIPTION OF THE INVENTION

Unless indicated otherwise, all ingredient amounts expressed in percentage terms are presented as % w/w.

The UV absorbers of the present invention have the structure shown in formula I.

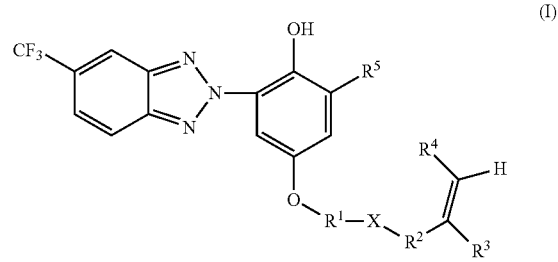

(I)

wherein:
$R^1 = C_1-C_{12}$ alkylene, $(CH_2CH_2O)_n$, $(CH_2CH(CH_3)O)_n$, or $CH_2CH_2CH_2(Si(CH_3)_2O)_bSi(CH_3)_2CH_2CH_2CH_2$;
X is nothing if $R^1$ is $(CH_2CH_2O)$, or $(CH_2CH(CH_3)O)_n$, or if $R^2$ is $Si(CH_3)_2$, otherwise X is O, NR, or S;
R=H, $CH_2Si(CH_3)_3$, $C_1-C_6$ alkyl, or phenyl;
$R^2$=nothing, $C(=O)$, $C(=O)C_jH_{2j}$, $C_1-C_6$ alkylene, phenyl, $C_1-C_6$ alkylphenyl, or $Si(CH_3)_2$;
$R^3$=H or $CH_3$;
$R^4$=H, $C_1-C_6$ alkyl, or phenyl;
$R^5=C_4-C_{12}$ t-alkyl;
b=1-9;
n=10; and
j=1-6.
Preferably,
  $R^1=C_1-C_6$ alkylene;
  X is O or NR;
  R=H or $C_1-C_6$ alkyl;
  $R^2=C(=O)$ or $C_1-C_6$ alkylphenyl;
  $R^3$=H or $CH_3$;
  $R^4$=H; and
  $R^5=C_4-C_6$ t-alkyl.
Most preferably,
  $R^1=C_2-C_3$ alkylene;
  X is O;
  $R^2=C(=O)$;
  $R^3$=H or $CH_3$;
  $R^4$=H; and
  $R^5$=t-butyl.

Compounds of formula (I) can be prepared using methods known in the art. For example, the most preferred compound of the present invention, which is 2-[2'-hydroxy-3'-tert-butyl-5'-(3''-methacryloyloxy)propoxyphenyl]-5-trifluoromethyl- 2H-benzotriazole ("Compound 1"), can be synthesized using the synthetic pathway shown in Scheme 1 below. This pathway starts with the trifluoromethyl-substituted 2-nitroaniline compound (I), which is converted to the diazonium salt (II) and azo coupled with 2-tert-butyl-4-(3'-hydroxypropoxy) phenol (III) followed by reduction of the nitro azo intermediate (IV) with glucose and zinc powder, which closes the benzotriazole ring providing the desired trifluoromethyl-substituted benzotriazole compound (V). In the final step of the synthesis (not shown in Scheme 1), the polymerizable group, such as a methacrylate group, may be incorporated by methods known in the art. Using this same synthetic pathway other trifluoromethyl-substituted benzotriazole compounds of Formula (I) can also be prepared.

Azo Coupling Reaction and Ring Closing Reduction to Form the Trifluoromethyl Benzotriazole Synthetic Products

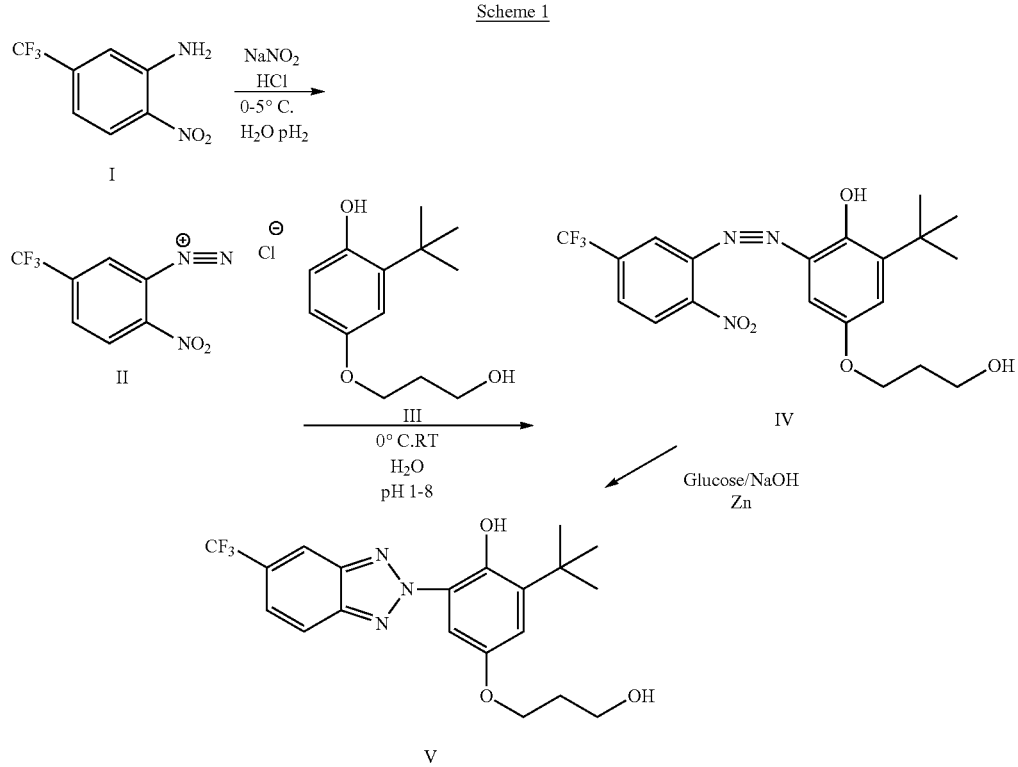

sitions of the present invention. Preferably, the ophthalmic device materials comprise an acrylic or methacrylic device-forming monomer. More preferably, the device-forming monomers comprise a monomer of formula (II):

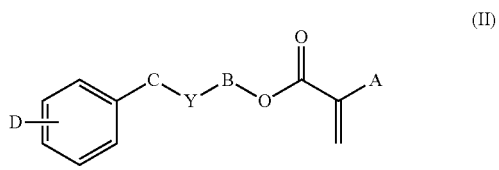

where in formula II:
A is H, $CH_3$, $CH_2CH_3$, or $CH_2OH$;
B is $(CH_2)_m$ or $[O(CH_2)_2]_z$;
C is $(CH_2)_w$;

m is 2-6;
z is 1-10;
Y is nothing, O, S, or NR', provided that if Y is O, S, or NR', then B is $(CH_2)_m$;
R' is H, $CH_3$, $C_nH_{2n'+1}$ (n'=1-10), iso-$OC_3H_7$, $C_6H_5$, or $CH_2C_6H_5$;
w is 0-6, provided that m+w≤8; and
D is H, $C_1$-$C_4$ alkyl, $C_1$-$C_4$ alkoxy, $C_6H_5$, $CH_2C_6H_5$ or halogen.

Preferred monomers of formula (II) are those wherein A is H or $CH_3$, B is $(CH_2)_m$, m is 2-5, Y is nothing or O, w is 0-1, and D is H. Most preferred are 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

The UV absorbers of the present invention are particularly suitable for use in IOLs. IOL materials will generally contain from 0.05 to 5% (w/w) of a UV absorber of formula (I). Preferably, IOL materials will contain from 0.1 to 2% (w/w), and most preferably, from 0.5-2% (w/w) of a UV absorber of formula (I).

Ophthalmic device materials are prepared by copolymerizing the UV absorbers of the present invention with other ingredients, such as device-forming materials, cross-linking agents, and blue-light blocking chromophores.

Many device-forming monomers are known in the art and include both acrylic and silicone-containing monomers among others. See, for example, U.S. Pat. Nos. 7,101,949; 7,067,602; 7,037,954; 6,872,793; 6,852,793; 6,846,897; 6,806,337; 6,528,602; and 5,693,095. In the case of IOLs, any known IOL device material is suitable for use in the compo- Monomers of formula (II) are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to a UV absorber of formula (I) and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2=C(CH_3)C(=O)O—(CH_2CH_2O)_p—C(=O)C(CH_3)=CH_2$ where p=1-50; and $CH_2=C(CH_3)C(=O)O(CH_2)_tO—C(=O)C(CH_3)=CH_2$ where t=3-20; and their corresponding acrylates. A preferred cross-linking monomer is $CH_2=C(CH_3)C(=O)O—(CH_2CH_2O)_p—C(=O)C(CH_3)=CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 0.1-17% (w/w).

Suitable polymerization initiators for device materials containing a UV absorber of the present invention include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.). Initiators are typically present in an amount of about 5% (w/w) or less. Because free-radical initiators do not become chemically a part of the polymers formed, the total amount of initiator is customarily not included when determining the amounts of other ingredients.

The device materials containing a UV absorber of the present invention may also contain a reactive colorant. Suitable reactive blue-light absorbing compounds include those described in U.S. Pat. No. 5,470,932. Blue-light absorbers are typically present in an amount from about 0.01-0.5% (weight).

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

The invention will be further illustrated by the following examples, which are intended to be illustrative, but not limiting.

Example

Acrylic Lens Materials Containing Compound 1

A monomer diluent formulation consisting of 2-phenylethyl acrylate (PEA), 2-hydroxyethyl methacrylate (HEMA), and 1,4-butanediol diacrylate (BDDA) was prepared by mixing the three monomers together in the proportions of 65:30:3.2 parts by weight. Formulations containing 0.6, 1.2, and 1.95% of Compound 1 were prepared by dissolving 0.012, 0.024, 0.039 grams of Compound 1, weighed to an accuracy of ±0.1 mg, into PEA/HEMA/BDDA monomer diluent to make 2 grams of each formulation. Just prior to curing, to each formulation was added 0.5% azo-bis-(iso-butyrnitrile) initiator (AIBN), by dissolving approximately 0.010 g into each formulation with mixing on a vortex mixer until fully dissolved.

Two comparison formulations containing other UV absorbers were also prepared. The first formulation had 1.8% of ortho-methallyl Tinuvin (2-[2'-hydroxy-3'-(2"-methyl-prop-2"-ene)-5'-methylphenyl]-2H-benzotriazole) ("Comparative Compound A") and was prepared by dissolving 0.036 grams of Comparative Compound A into 1.964 grams of the PEA/HEMA/BDDA monomer diluent. Just prior to curing, 1.8% bis-(4-tert-butylcyclohexylperoxy) dicarbonate initiator (Perkadox-16) was added (0.036 grams) and the formulation was mixed on a vortex mixer until fully dissolved.

Likewise, the second comparison formulation containing 1.51% of 2-{2'-hydroxy-3'-methacryloyloxymethyl-5'-methoxyphenyl}-5-trifluoromethyl-2H-benzotriazole ("Comparative Compound B") was prepared by dissolving 0.0302 grams of Comparative Compound B into 1.9698 grams of PEA/HEMA/BDDA monomer diluent. Just prior to curing, 0.5% AIBN initiator was added (0.010 g) and the formulation was mixed on a vortex mixer until fully dissolved.

After mixing, each formulation was passed through a 0.45 μm membrane syringe filter and purged with nitrogen. Then, each formulation was cast into polypropylene molds to form 1×2-cm×~1-mm rectangular films by thermal curing. The samples initiated with AIBN were cured at 90° C. for 1 hour, followed by a post-cure of 2 hours at 100° C.; the samples initiated with Perkadox-16 were cured at 80° C. for 2 hours, followed by a post-cure at 100° C. for 2 hours. All samples were cured in a programmable temperature oven (1000 Halfo Series, VWR Scientific Corp.). The films were demolded and placed into polypropylene tissue capsules, then extracted at room temperature with acetone for about 16 hours. Following extraction, the films were slowly dried in air and then dried under vacuum at 60° C. to remove residual acetone. Finally, the film samples were analyzed by UV-Visible transmission spectroscopy from 800-300 nm using a Perkin-Elmer Lambda 35 instrument equipped with a Lab Sphere RSA-PE-20 integrating sphere.

The formulations containing Compound 1 exhibited pronounced 1% and 10% transmission cutoffs as compared to the two reference formulations (containing 1.8% Comparative Compound A and 1.51% Comparative Compound B UV absorbers, respectively). The results are shown in Table 1. The 10% transmission cutoffs were in the wavelength range of 434 to 446.5 nm for the materials containing Compound 1. The transmission spectra for the tested formulations are shown in FIG. 1.

TABLE 1

| UV Absorber | Molecular Weight | Concentration | | Wavelength (nm) | |
|---|---|---|---|---|---|
| | | wt. % | mmoles/g | 1% T | 10% T |
| Compound 1 | 477.48 | 0.6 | 0.013 | 423.0 | 434.0 |
| | | 1.2 | 0.025 | 433.0 | 441.0 |
| | | 1.95 | 0.041 | 438.5 | 446.5 |
| Comparative Compound B | 407.35 | 1.51 | 0.037 | 429.0 | 435.5 |
| Comparative Compound A | 279.34 | 1.8 | 0.064 | 400.0 | 395.0 |

Compound 1 has a transmission cutoff at higher wavelengths of blue light than the Comparative Compound A and Comparative Compound B UV absorbers. The data shown in Table 1 demonstrates the ability of Compound 1 to absorb short-wavelength blue (violet) light more effectively than the other two UV absorbers tested.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

We claim:

1. A UV absorber of the formula

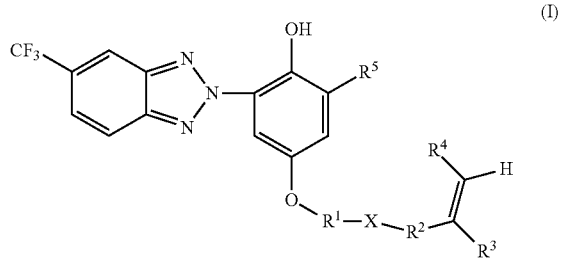

(I)

wherein
is $R^1$=$C_1$-$C_{12}$ alkylene, $(CH_2CH_2O)_n$, $(CH_2CH(CH_3)O)_n$, or $CH_2CH_2CH_2(Si(CH_3)_2O)_bSi(CH_3)_2CH_2CH_2CH_2$;
X is nothing if $R^1$ is $(CH_2CH_2O)_n$, $(CH_2CH(CH_3)O)_n$, or $R^2$ is $Si(CH_3)_2$, otherwise X is O, NR, or S;
R=H, $CH_2Si(CH_3)_3$, $C_1$-$C_6$ alkyl, or phenyl;
$R^2$=nothing, C(=O), C(=O)$C_jH_{2j}$, $C_1$-$C_6$ alkylene, phenyl, $C_1$-$C_6$ alkylphenyl, or $Si(CH_3)_2$;
$R^3$=H or $CH_3$;
$R^4$=H, $C_1$-$C_6$ alkyl, or phenyl;
$R^5$=$C_4$-$C_{12}$ t-alkyl;
b=1-9;
n=1-10; and
j=1-6.

2. The UV absorber of claim 1, wherein
$R^1$=$C_1$-$C_6$ alkylene;
X is O or NR;
R=H or $C_1$-$C_6$ alkyl;
$R^2$=C(=O) or $C_1$-$C_6$ alkylphenyl;
$R^3$=H or $CH_3$;
$R^4$=H; and
$R^5$=$C_4$-$C_6$ t-alkyl.

3. The UV absorber of claim 2, wherein
$R^1$=$C_2$-$C_3$ alkylene;
X is O;
$R^2$=C(=O);
$R^3$=H or $CH_3$;
$R^4$=H; and
$R^5$=t-butyl.

4. The UV absorber of claim 3, wherein the UV absorber is 2-[2'-hydroxy-3'-tert-butyl-5'-(3"-methacryloyloxy)propoxyphenyl]-5-trifluoromethyl-2H-benzotriazole.

5. An ophthalmic device material comprising the UV absorber of claim 1 and a device-forming monomer selected from the group consisting of acrylic monomers and silicone-containing monomers.

6. The ophthalmic device material of claim 5, wherein the ophthalmic device material comprises from 0.05 to 5% w/w of the UV absorber.

7. The ophthalmic device material of claim 6, wherein the ophthalmic device material comprises from 0.1 to 2% w/w of the UV absorber.

8. The ophthalmic device material of claim 7, wherein the ophthalmic device material comprises from 0.5 to 2% w/w of the UV absorber.

9. The ophthalmic device material of claim 5, wherein the ophthalmic device material comprises a device-forming monomer of formula [II]:

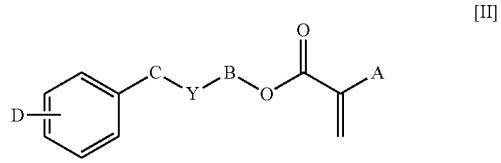

[II]

wherein formula [II]:
A is H, $CH_3$, $CH_2CH_3$, or $CH_2OH$;
B is $(CH_2)_m$ or $[O(CH_2)_2]_z$;
C is $(CH_2)_w$;
m is 2-6;
z is 1-10;
Y is nothing, O, S, or NR', provided that if Y is O, S, or NR', then B is $(CH_2)_m$;
R' is H, $CH_3$, $C_nH_{2n'+1}$ (n'=1-10), iso-$OC_3H_7$, $C_6H_5$, or $CH_2C_6H_5$;
w is 0-6, provided that m+w≤8; and
D is H, $C_1$-$C_4$ alkyl, $C_1$-$C_4$ alkoxy, $C_6H_5$, $CH_2C_6H_5$ or halogen.

10. The ophthalmic device material of claim 9, wherein in formula [II]:
A is H or $CH_3$;
B is $(CH_2)_m$;
m is 2-5;
Y is nothing or O;
w is 0-1; and
D is H.

11. The ophthalmic device material of claim 10, wherein the ophthalmic device material comprises a monomer selected from the group consisting of: 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

12. The ophthalmic device material of claim 5, wherein the ophthalmic device material comprises a cross-linking agent.

13. The ophthalmic device material of claim 5, wherein the ophthalmic device material comprises a reactive blue-light absorbing compound.

14. An ophthalmic device comprising the ophthalmic device material of claim 5.

15. The ophthalmic device of claim 14, wherein the ophthalmic device is selected from the group consisting of an intraocular lens; a contact lens; a keratoprosthesis; and a corneal inlay or ring.

* * * * *